US 6,348,047 B1

(12) United States Patent
Harper

(10) Patent No.: US 6,348,047 B1
(45) Date of Patent: Feb. 19, 2002

(54) FEMININE HYGIENE ARTICLE WITH UPSTANDING MEMBER

(76) Inventor: Vernice J. Harper, 3986 Southclare Rd., Baltimore, MD (US) 21213

( * ) Notice: Subject to any disclaimer, the term of this patent is extended or adjusted under 35 U.S.C. 154(b) by 0 days.

(21) Appl. No.: 09/522,499

(22) Filed: Mar. 10, 2000

(51) Int. Cl.[7] ............................................. A61F 13/20
(52) U.S. Cl. ...................... 604/385.17; 604/385.01; 604/385.101; 604/385.03
(58) Field of Search ................ 604/385.01, 385.101, 604/385.17, 385.03, 11, 378, 384, 386, 387, 401, 389

(56) References Cited

U.S. PATENT DOCUMENTS

| | | | |
|---|---|---|---|
| 2,092,346 A | | 9/1937 | Arone |
| 3,183,909 A | * | 5/1965 | Roehr .................... 128/290 |
| 3,420,234 A | | 1/1969 | Phelps |
| 3,905,372 A | | 9/1975 | Denkinger |
| 4,023,571 A | * | 5/1977 | Comerford et al. ......... 128/290 |
| D266,873 S | | 11/1982 | Riedell |
| 4,533,357 A | * | 8/1985 | Hall ............................ 609/401 |
| 4,804,380 A | * | 2/1989 | Lassen et al. .......... 604/385.01 |
| 5,057,096 A | * | 10/1991 | Faglione ................. 604/385.01 |
| 5,290,262 A | * | 3/1994 | Vukos et al. .......... 604/385.01 |
| 5,383,868 A | | 1/1995 | Hyun |
| 5,389,181 A | * | 2/1995 | Vukos et al. ................ 156/264 |
| 5,702,380 A | * | 12/1997 | Walker ................... 604/385.01 |
| 5,743,896 A | * | 4/1998 | Parker .................... 604/385.01 |
| 5,795,344 A | * | 8/1998 | Chappell ..................... 604/379 |
| 5,827,258 A | * | 10/1998 | McFall et al. ......... 604/385.01 |
| 5,833,680 A | * | 11/1998 | Hartman ................ 604/385.01 |
| 5,873,869 A | * | 2/1999 | Hammons et al. ..... 604/385.01 |
| 5,947,945 A | * | 9/1999 | Cree et al. ................... 604/368 |
| 6,059,763 A | * | 5/2000 | Brown ................... 604/385.01 |
| 6,100,442 A | * | 8/2000 | Samuelsson et al. ....... 604/378 |
| 2001/0003157 A1 | * | 6/2001 | Toth ........................... 606/197 |

* cited by examiner

Primary Examiner—John G. Weiss
Assistant Examiner—Michele Kidwell

(57) ABSTRACT

A feminine hygiene article for directing menstrual flow into a panel. The feminine hygiene article includes a base panel for absorbing moisture. The base panel has a top surface and a bottom surface. An upstanding member directs flow of the moisture. The upstanding member has a top side, a bottom side and a peripheral wall extending therebetween. The bottom side is fixedly coupled to the top surface of the base panel. A sealing member has a front side and a back side. The front side is fixedly coupled to the bottom surface of the base panel.

1 Claim, 2 Drawing Sheets

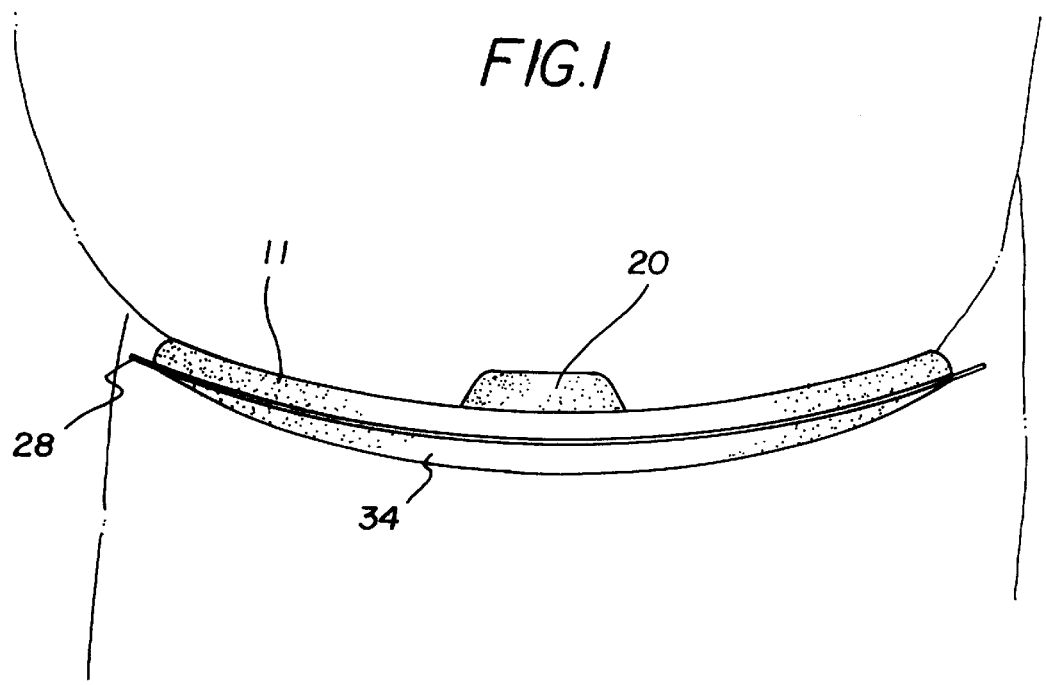
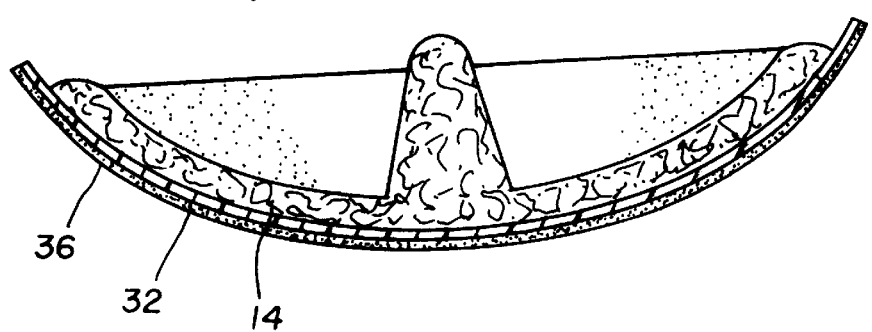

FEMININE HYGIENE ARTICLE WITH UPSTANDING MEMBER

BACKGROUND OF THE INVENTION

1. Field of the Invention

The present invention relates to feminine hygiene articles and more particularly pertains to a new feminine hygiene article for directing menstrual flow into a panel.

2. Description of the Prior Art

The use of feminine hygiene articles is known in the prior art. More specifically, feminine hygiene articles heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 2,092,346; U.S. Pat. No. 5,383,868; U.S. Pat. No. 3,905,372; U.S. Pat. No. 5,290,262; U.S. Pat. No. 3,420,234; and U.S. Des. Pat. No. 266,873.

While these devices fulfill their respective, particular objectives and requirements, the aforementioned patents do not disclose a new feminine hygiene article. The inventive device includes a base panel for absorbing moisture. The base panel has a top surface and a bottom surface. An upstanding member directs flow of the moisture. The upstanding member has a top side, a bottom side and a peripheral wall extending therebetween. The bottom side is fixedly coupled to the top surface of the base panel. A sealing member has a front side and a back side. The front side is fixedly coupled to the bottom surface of the base panel.

In these respects, the feminine hygiene article according to the present invention substantially departs from the conventional concepts and designs of the prior art, and in so doing provides an apparatus primarily developed for the purpose of directing menstrual flow into a panel.

SUMMARY OF THE INVENTION

In view of the foregoing disadvantages inherent in the known types of feminine hygiene articles now present in the prior art, the present invention provides a new feminine hygiene article construction wherein the same can be utilized for directing menstrual flow into a panel.

The general purpose of the present invention, which will be described subsequently in greater detail, is to provide a new feminine hygiene article apparatus and method which has many of the advantages of the feminine hygiene articles mentioned heretofore and many novel features that result in a new feminine hygiene article which is not anticipated, rendered obvious, suggested, or even implied by any of the prior art feminine hygiene articles, either alone or in any combination thereof.

To attain this, the present invention generally comprises a base panel for absorbing moisture. The base panel has a top surface and a bottom surface. An upstanding member directs flow of the moisture. The upstanding member has a top side, a bottom side and a peripheral wall extending therebetween. The bottom side is fixedly coupled to the top surface of the base panel. A sealing member has a front side and a back side. The front side is fixedly coupled to the bottom surface of the base panel.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new feminine hygiene article apparatus and method which has many of the advantages of the feminine hygiene articles mentioned heretofore and many novel features that result in a new feminine hygiene article which is not anticipated, rendered obvious, suggested, or even implied by any of the prior art feminine hygiene articles, either alone or in any combination thereof.

It is another object of the present invention to provide a new feminine hygiene article which may be easily and efficiently manufactured and marketed.

It is a further object of the present invention to provide a new feminine hygiene article which is of a durable and reliable construction.

An even further object of the present invention is to provide a new feminine hygiene article which is susceptible of a low cost of manufacture with regard to both materials and labor, and which accordingly is then susceptible of low prices of sale to the consuming public, thereby making such feminine hygiene article economically available to the buying public.

Still yet another object of the present invention is to provide a new feminine hygiene article which provides in the apparatuses and methods of the prior art some of the advantages thereof, while simultaneously overcoming some of the disadvantages normally associated therewith.

Still another object of the present invention is to provide a new feminine hygiene article for directing menstrual flow into a panel.

Yet another object of the present invention is to provide a new feminine hygiene article which includes a base panel for absorbing moisture. The base panel has a top surface and a bottom surface. An upstanding member directs flow of the moisture., The upstanding member has a top side, a bottom side and a peripheral wall extending therebetween. The bottom side is fixedly coupled to the top surface of the base panel. A sealing member has a front side and a back side. The front side is fixedly coupled to the bottom surface of the base panel.

Still yet another object of the present invention is to provide a new feminine hygiene article that is less intrusive than standard feminine hygiene products.

Even still another object of the present invention is to provide a new feminine hygiene article that pulls the moisture of menstrual flow away from the body and into a panel.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic side view of a new feminine hygiene article according to the present invention.

FIG. 3 is a schematic cross-sectional end view of the present invention.

DESCRIPTION OF THE PREFERRED EMBODIMENT

Figure 2:
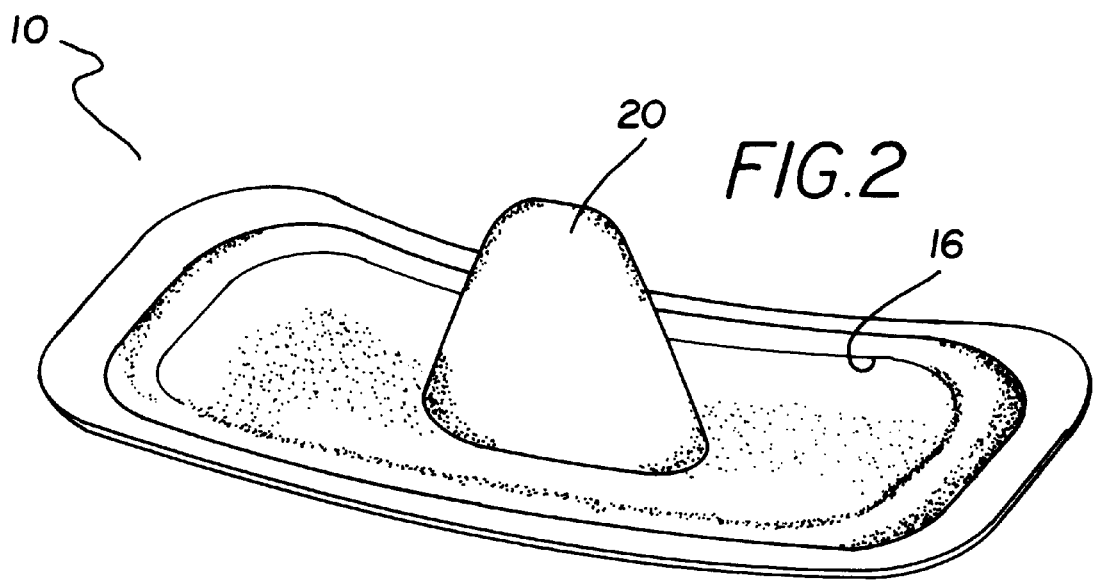
FIG. 2 is a schematic perspective view of the present invention.
Figure 4:
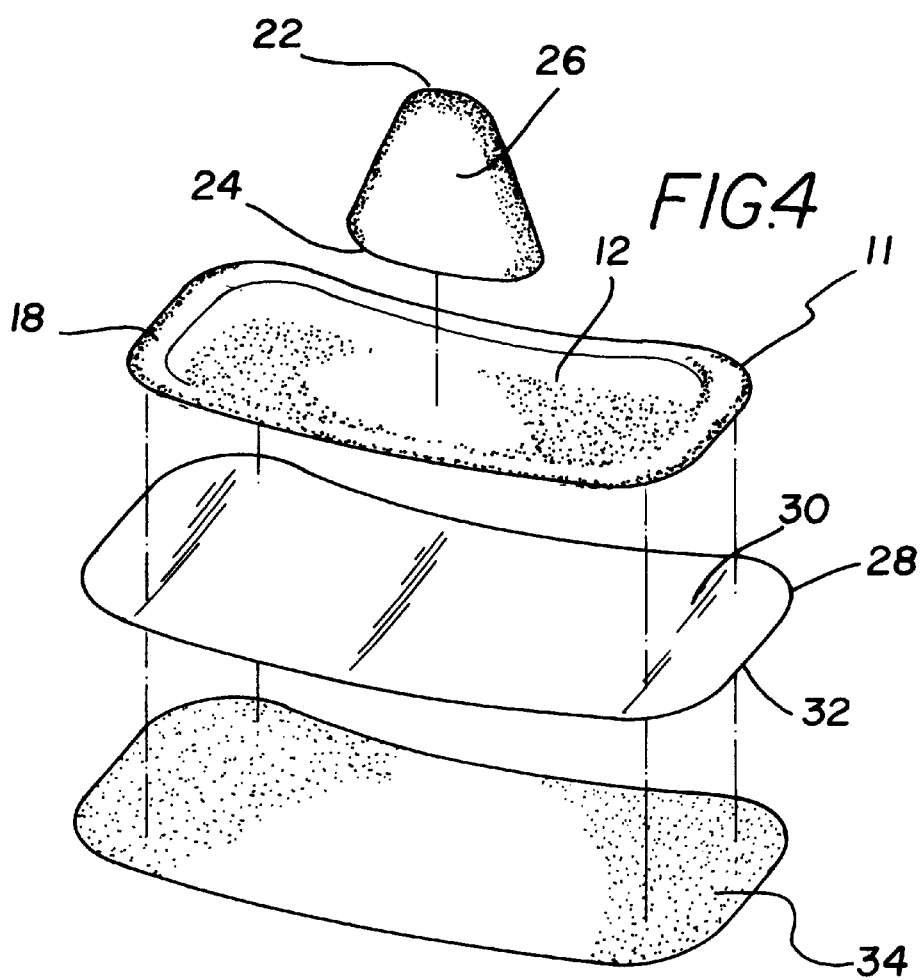
FIG. 4 is a schematic perspective view of the present invention.

With reference now to the drawings, and in particular to FIGS. 1 through 4 thereof, a new feminine hygiene article embodying the principles and concepts of the present invention and generally designated by the reference numeral 10 will be described.

As best illustrated in FIGS. 1 through 4, the feminine hygiene article 10 generally comprises a base panel 11 for absorbing moisture. The base panel 11 has a top surface 12 and a bottom surface 14. The base panel 11 has a peripheral edge 16. A lip 18 is coupled to and extends upwardly away from the peripheral edge 16. The base panel 11 is preferably comprised of a cotton material. The base panel 11 has a generally rectangular shape, and ideally a height between one-half inches and three-fourth inches. The base panel 11 has a length between five and eight inches.

An upstanding member 20 directs flow of moisture. The upstanding member 20 has a top side 22, a bottom side 24 and a peripheral wall 26 extending therebetween. The bottom side 24 is fixedly coupled to the top surface 12 of the base panel 11. The upstanding member 20 is located in a central portion of the base panel 11. The bottom side 24 has a longitudinal axis orientated generally parallel to a longitudinal axis of the base panel 11. The top side 22 preferably has a convex shape. A length of the base side 24 has a length preferably twice as long as a width of the top side 22. The peripheral wall 26 has a height approximately between one and two inches A sealing member 28 has a side 30 and a side 32. The side 30 is fixedly coupled to the bottom surface 14 of the base panel 11. The sealing member 28 has a size and shape is substantially identical to the bottom surface 14 of the base panel 11. The sealing member 28 ideally comprises a flexible plastic. The sealing member 28 is liquid impermeable.

An adhesive member 34 removably attaches the sealing member 28 to the undergarments of the user. The adhesive member 34 is fixedly coupled to the back side 32 of the sealing member 28. The adhesive member 34 has an adhesive side 36 directed away from the sealing member 28. The adhesive member 34 covers a substantial portion of a surface of the back side of the sealing member 28.

In use, the adhesive member 34 is removably coupled to the inside portion of a woman's underwear. The upstanding member 20 is then placed in the vagina. Menstrual flow will be directed through the upstanding member 20 and to the base panel 11. The sealing member 28 prevents the menstrual flow from reaching the underwear of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A feminine hygiene article, said article being placeable between the body of the user and undergarments worn by the user, said article comprising:

a base panel for absorbing moisture and having opposite ends, said base panel having a top surface and a bottom surface, said base panel having a peripheral edge, a lip being coupled to and extending upwardly away from said peripheral edge, said base panel being comprised of a cotton material, said base panel having a generally rectangular shape, said base panel having a height generally between one-half inches and three-quarter inches;

an upstanding member for directing flow of the moisture, said upstanding member having a top side, a bottom side and a peripheral wall extending therebetween, said bottom side being fixedly coupled to said top surface of said base panel, said upstanding member being located in a central portion of said base panel, said upstanding member being elongated towards the opposite ends of the base panel, said bottom side having a longitudinal axis orientated generally parallel to a longitudinal axis of said base panel, said top side having a generally convex shape, a length of said base side having a length being approximately twice as long as a width of said top side, said peripheral wall having a height substantially equal to one and one-half inches; and a sealing member, said sealing having a front side and a back side, said front side being fixedly coupled to said bottom surface of said base panel, said sealing member having a size and shape being substantially identical to said bottom surface of said base panel, said sealing member comprising a plastic, said sealing member being liquid impermeable;

an adhesive member for removably attaching said sealing member to the undergarments of the user, said adhesive member being fixedly coupled to said back side of said sealing member, said adhesive member having an adhesive side being directed away from said sealing member, said adhesive member covering a substantial portion of a surface of said back side of said sealing member;

wherein the perimeter of said base panel lies generally in a plane, and wherein portions of said base panel lateral to said upstanding member curve upwardly from the bottom side of the upstanding member such that an uppermost tip of the upstanding member lies generally in the plane of said perimeter; and wherein a height is defined between the bottom surface of said base panel and the uppermost tip of said upstanding member, and a width is defined between opposite points on said perimeter in the plane of said perimeter, and said height is approximately one-quarter of said width.

* * * * *